US007288269B2

(12) United States Patent
Wang

(10) Patent No.: US 7,288,269 B2
(45) Date of Patent: Oct. 30, 2007

(54) ASAFETIDA EXTRACT AS MEDICINE FOR ABSTINENCE OF DRUGS

(75) Inventor: Zemin Wang, Qionglai (CN)

(73) Assignee: Yanding Wang, Quionglai, P.R. (CN)

( * ) Notice: Subject to any disclaimer, the term of this patent is extended or adjusted under 35 U.S.C. 154(b) by 392 days.

(21) Appl. No.: 10/965,698

(22) Filed: Oct. 13, 2004

(65) Prior Publication Data

US 2006/0078570 A1    Apr. 13, 2006

(51) Int. Cl.
*A01N 65/00* (2006.01)
(52) U.S. Cl. .................. 424/725; 424/195.18; 514/810
(58) Field of Classification Search ...................... None
See application file for complete search history.

(56) References Cited

FOREIGN PATENT DOCUMENTS

RU          2161038 C1 * 12/2000

OTHER PUBLICATIONS

Ramezani, M. et al. Journal of Ethnopharmacology (2001), 77: 71-75. Effects of *Ferula gummosa* Boiss. fractions on morphine dependence in mice.*
Lingford-Hughes, A. et al. British Journal of Psychiatry (2003), 182: 97-100. Neurobiology of addiction and implications for treatment.*
Wiley, J. L. et al. Life Sciences (2003), 72: 3023-3033. Evaluation of toluene dependence and cross-sensitization to diazepam.*
Zacny, J. P. et al. Pharmacology Biochemistry & Behavior (1994), 49(3): 575-578. Effects of naloxone on the subjective and psychomotor effects of nitrous oxide in humans*

Sukhotina, I. A. et al. Behaviour Pharmacology (May 2004), 15(3): 207-214. Caffeine withdrawal syndrome in social interaction test in mice: Effects of the NMDA receptor channel blockers, memantine and neramexane.*
(1978) "National Chinese herbal medicine compilation", published by Renmin Sanitation Press, vol. 2, p. 318.
(2000) "Pharmacopoeia of the People's Republic of China" Part 1, p. 148.

* cited by examiner

*Primary Examiner*—Michele C. Flood
(74) *Attorney, Agent, or Firm*—Knobbe, Martens, Olson & Bear, LLP

(57) ABSTRACT

An asafetida extract in the preparation of medicine for abstinence of drugs. A method for abstinence of drugs, which comprises administering a therapeutically effective amount of asafetida extract to subjects. The asafetida extract may be extracted from factice resin of *Ferula sinkiangensis* K. M. Shen or *Ferula fukanensis* K.M. Shen, and consists essentially of α-pinene, α-terpinene, 2-borneol, terpin-4-ol, D-fenchyl alcohol, pinocarveol, β-ocimene A, β-ocimene B, di-sec-butyl disulfide, sec-butyl-trans-1-butenyl disulfide, sec-butyl-cis-propenyl disulfide, sec-butyl-cis-1-butenyl disulfide, sec-butyl-trans-2-butenyl disulfide and thio-sec-butyl-trans-methylethenyl disulfide. The asafetida extract may also be extracted from factice resin of *F. assafoetida* L from Iran and Afghanistan and the like, and consists essentially of α-pinene, 2-borneol, terpin-4-ol, D-fenchyl alcohol, pinocarveol, dimethyl disulfide, dimethyl trisulfide, methylpropenyl disulfide, 2,2-dimethylthiopropane, 1,2-diethylthiopropane, N,N-dimethylthioformamide and propenylbutyl disulfide. The medicine for abstinence of drugs prepared with asafetida extract is suitable for the use in the abstinence treatment of subjects addicted to opioid, morphine, marijuana, diamorphine and the like.

4 Claims, No Drawings

ASAFETIDA EXTRACT AS MEDICINE FOR ABSTINENCE OF DRUGS

FIELD OF THE INVENTION

The present invention relates to the use of asafetida extract as a medicine for abstinence of drugs.

BACKGROUND OF THE INVENTION

Asafetida is a secretion of natural plant. According to "Pharmacopoeia of the People's Republic of China", edited in 2000, page 148, Part I, the asafetida is described as: bitter in taste, pungent, warm, going through spleen and stomach channel; eliminating stagnated food, dispelling cold, destroying intestinal worms and used for stagnated meat food, gore lump, abdomen lump, abdominal pain due to enterositosis. According to "National Chinese herbal medicine compilation", published by Renmin Sanitation Press, 1978, Vol. 2, p. 318 the asafetida is described as: bitter in taste, tepefaction, eliminating stagnated food, destroying intestinal worms and dispelling cold; effective in the treatment of malnutrition due to parasitic infestation, abdominal mass, distending pain in stomach and abdomen, malaria and diarrhea, and also effective in preventing measles. Asafetida is conventionally used as water decoction or pill, wherein the special strong odor of asafetida is difficult to be covered up and therefore limits its application. Use of modern preparation technology may cover up or weaken the special odor of asafetida. Therefore, there has been asafetida extract prepared by conventional methods from Chinese asafetida or asafetida from other countries, the extract being volatile oil or supersaturated aqueous solution of volatile oil.

Addictive drugs impair health of human body, seriously influence the stability of family and society, and is one of the sources of plunder, violence, degeneration and homicide. The drug abuse is a serious worldwide problem endangering human being. Some chemical drugs have been used as medicine for abstinence of drugs for a long time, e.g., phenoxyimidazoline hydrochloride (clonidine), methadone, barbiturates and other sedative hypnotics. These pharmaceutical chemicals are also narcotics or psychotropics, and may result in drug dependence. In addition, these chemicals may bring about many side effects in case of long-term use.

SUMMARY OF THE INVENTION

The present invention provides the use of asafetida extract in the preparation of medicine for abstinence of drugs. The medicine for abstinence of drugs is in a form selected from the group consisted of injection, capsule, drop pill, tablet, granule, powder, oral liquid and the like.

The present invention further provides a method for abstinence of drugs, which comprises administering a therapeutically effective amount of asafetida extract to subjects. In the present invention, the asafetida extract may be administrated in a form selected from the group consisted of injection, capsule, drop pill, tablet, granule, powder, oral liquid and the like.

In the present invention, the term "therapeutically effective amount of asafetida extract" refers to the amount of asafetida extract sufficient for producing an effect of abstinence of morphine. Commonly, the effective amount of asafetida extract is 0.1-20 g, preferably 1-3 g (equivalent to the amount of original crude material).

The asafetida extract according to the present invention may be extracted from factice resin of *Ferula sinkiangensis* K. M. Shen or *Ferula fukanensis* K. M. Shen, and consisted essentially of α-pinene, α-terpinene, 2-borneol, terpin-4-ol, D-fenchyl alcohol, pinocarveol, β-ocimene A, β-ocimene B, di-sec-butyl disulfide, sec-butyl-trans-1-butenyl disulfide, sec-butyl-cis-propenyl disulfide, sec-butyl-cis-1-butenyl disulfide, sec-butyl-trans-2-butenyl disulfide and thio-sec-butyl-trans-methylethenyl disulfide.

The asafetida extract according to the present invention may also be extracted from factice resin of *F. assafoetida* L from Iran, Afghanistan and the like, and consisted essentially of α-pinene, 2-borneol, terpin-4-ol, D-fenchyl alcohol, pinocarveol, dimethyl disulfide, dimethyl trisulfide, methylpropenyl disulfide, 2,2-dimethylthiopropane, 1,2-diethylthiopropane, N,N-dimethylthioformamide and propenylbutyl disulfide.

DETAILED DESCRIPTION OF THE PREFERRED EMBODIMENT

When drugs and narcotics enter human body, they bind with morphine receptor existing in some domains inside human brain and produce a series of euphoria sensations. Once the drugs are quitted, a series of abstinence syndromes are produced in the same manner. The inventors have conducted intensive experimental study and found asafetida extract has a regulatory effect on central nervous system. The effective ingredients in asafetida extract enter into human body and then combine with morphine receptor existing in human brain to maintain normal function of nerve cells, thereby resulting in the remission and even disappearance of abstinence syndrome, stopping drug addiction. Asafetida extract therefore can be used in the preparation of medicine for abstinence of drugs.

Asafetida extract may be prepared by conventional methods from the factice resin of *Ferula sinkiangensis* K. M. Shen or *Ferula fukanensis* K. M. Shen, the extract being volatile oil or supersaturated aqueous solution of volatile oil, pH 4-5.7. Above asafetida extracts were analyzed by GC-MS detection at Chengdu Analytic and Test Center of Chinese Academy of Sciences. The results demonstrated all of these asafetida extracts consisted essentially of α-pinene, α-terpinene, 2-borneol, terpin-4-ol, D-fenchyl alcohol, pinocarveol, β-ocimene A, β-ocimene B, di-sec-butyl disulfide, sec-butyl-trans-1-butenyl disulfide, sec-butyl-cis-propenyl disulfide, sec-butyl-cis-1-butenyl disulfide, sec-butyl-trans-2-butenyl disulfide and thio-sec-butyl-trans-methylethenyl disulfide.

Asafetida extract may also be prepared by conventional methods from the factice resin of *F. assafoetida* L from Iran, Afghanistan and the like, the extract being volatile oil or supersaturated aqueous solution of volatile oil, pH 4-5.7. Above asafetida extracts was analyzed by GC-MS detection at Chengdu Analytic and Test Center of Chinese Academy of Sciences. The results demonstrated all of these asafetida extracts consisted essentially of α-pinene, 2-borneol, terpin-4-ol, D-fenchyl alcohol, pinocarveol, dimethyl disulfide, dimethyl trisulfide, methylpropenyl disulfide, 2,2-dimethylthiopropane, 1,2-diethylthiopropane, N,N-dimethylthioformamide and propenylbutyl disulfide.

Asafetida extract may be prepared by conventional oil-water separation, water vapor distillation, azeotropic distillation, vacuum distillation or solvent extraction.

With regard to the oil-water separation, azeotropic distillation or water vapor distillation may be applied and volatile oil is separated by oil-water separator. 0.1-80 parts by weight of purified water is added to 0.1-20 parts by weight of asafetida and the azeotropic distillation or water vapor distillation is performed at 105-108° C. 0.012-2.4 parts by weight of volatile oil is collected after oil-water separation (assuming average content of volatile oil in crude material is 12%).

With regard to the water vapor distillation, 0.1-80 parts by weight of purified water is added to 0.1-20 parts by weight of asafetida and the water vapor distillation is performed at 105-108° C. 0.2-240 parts by weight of forerunning liquid is collected and redistillation is performed. 0.1-200 parts by weight of redistillation liquid, i.e. asafetida extract, is obtained after collection.

With regard to the azeotropic distillation, 0.5-400 parts by weight of purified water is added to 0.1-20 parts by weight of asafetida and the azeotropic distillation is performed at 105-108° C. 0.2-240 parts by weight of forerunning liquid is collected and redistillation is performed. 0.1-200 parts by weight of redistillation liquid, i.e. asafetida extract, is obtained after collection.

With regard to the vacuum distillation, 0.5-400 parts by weight of purified water is added to 0.1-20 parts by weight of asafetida and the vacuum distillation is performed at 104-107° C. and pressure of 1300-1400 Pa. 0.2-240 parts by weight of forerunning liquid is collected and redistillation is performed. 0.1-200 parts by weight of redistillation liquid, i.e. asafetida extract, is obtained after collection.

With regard to the solvent extraction, 0.1-20 parts by weight of asafetida is added to 0.6-120 parts by weight of organic solvents such as ethanol and chloroform. Weight ratio of ethanol and chloroform is 2:1. Reflux extraction is performed at 65-70° C. for 2 hours. When the temperature of refluxing liquid drops to room temperature, the refluxing liquid is discharged and organic solvents are recovered. 0.1-80 parts by weight of purified water is added to obtained crude volatile oil and water vapor distillation is conducted at 105-108° C. 0.2-240 parts by weight of forerunning liquid is collected and then subjected to redistillation. 0.1-200 parts by weight of redistillation liquid, i.e. asafetida extract, is obtained after collection.

Above medicine for abstinence of drugs may be in a form selected from the group consisting of injection, capsule, drop pill, tablet, granule, powder, oral liquid and the like. The injection may be administrated intramuscularly or intravenously.

In order to understand the essence of present invention, the asafetida injection, asafetida capsule, asafetida tablet, and asafetida granule for abstinence of drugs are prepared from asafetida extract. The use of asafetida extract as a medicine for abstinence of drugs is demonstrated by animal experiment and clinical trial.

The medicine for abstinence of drugs prepared with asafetida extract: asafetida injection. Solubilizer such as 2,3-HP, β-CD (2,3-hydroxypropyl-β-cyclodextrin) is added to asafetida extract with agitation and isotonic adjusting agent NaCl (NaCl for injection) is then added. Water for injection is added to a defined amount and agitation is continued. After pH adjustment, resulting solution is filtered through membrane filter, filled into ampules and sealed. Asafetida injection is obtained after sterilization.

The medicine for abstinence of drugs prepared with asafetida extract: asafetida capsule. The weight ratio of asafetida volatile oil and excipient is 1: 3-20, wherein the excipient is at least one selected from starch, compressible starch, hydroxypropyl cellulose with low substitution degree (L-HPC), microcrystalline cellulose, carboxymethyl starch sodium (CMS-Na). Excipients are placed into agitator and agitated for 5 min, then volatile oil is sprayed uniformly into excipients and agitation is continued for 5 min. 5% starch slurry is added to make a soft material, which is placed into a granulator and filtered through stainless steel sieve to form wet granules. The wet granules are dried below 60° C. and obtained dry granules are put into granulator again and filtered through stainless steel sieve to adjust the granules. In order to filling the capsule uniformly and smoothly, lubricant such as magnesium stearate is added and the weight ratio of excipient and lubricant is 1: 0.002-0.01. Dry granules after adjustment are put into agitator and lubricant is added to mix for 5 min, then asafetida capsules are made in a full automatic capsule filling machine. Asafetida extract in each asafetida capsule is equivalent to 0.1-1 g asafetida crude material.

The medicine for abstinence of drugs prepared with asafetida extract: asafetida tablet. The weight ratio of asafetida volatile oil and excipient is 1: 3-20, wherein the excipient is at least one selected from starch, compressible starch, L-HPC, microcrystalline cellulose, CMS-Na. Excipients are placed into agitator and agitated for 5 min, then volatile oil is sprayed uniformly into excipients and agitation is continued for 5 min. 5% starch slurry is added to make a soft material, which is placed into a granulator and filtered through stainless steel sieve to form wet granules. The wet granules are dried below 60° C. and obtained dry granules are put into granulator again and filtered through stainless steel sieve to adjust the granules. In order to tabletting uniformly and smoothly, lubricant such as magnesium stearate is added and the weight ratio of excipient and lubricant is 1:0.002-0.01. Dry granules after adjustment are put into agitator and lubricant is added to mix for 5 min, then asafetida tablets are made in a tablet machine. The asafetida tablets are then sent to a coating machine to form film coating. Asafetida extract in each asafetida tablet is equivalent to 0.1-1 g asafetida crude material.

The medicine for abstinence of drugs prepared with asafetida extract: asafetida granule. The weight ratio of asafetida volatile oil and excipient is 1:10-100, wherein the excipient is sucrose powder and dextrin. Excipients are placed into agitator and agitated for 5 min, then volatile oil is sprayed uniformly into adjuvant and agitation is continued for 5 min. 2% starch slurry is added to make a soft material, which is placed into a granulator and filtered through stainless steel sieve to form wet granules. The wet granules are dried below 60° C. and obtained dry granules are put into granulator again and filtered through stainless steel sieve to adjust the granules. Dry granules after adjustment are sent to a granule racking machine for packaging. Asafetida extract in each package of asafetida is equivalent to 0.1-2 g asafetida crude material.

Following are animal experiments and clinical trials on drugs abstinence effect of asafetida extract.

6 g of 2,3-HP, β-CD was added to 1000 ml of asafetida extract (aqueous solution of volatile oil, equivalent to 0.5 g/ml asafetida crude material) and agitated for 5 min. 7 g NaCl (NaCl for injection) was then added and agitation is continued for 5 min. Resulting solution was then adjusted to pH=5.46, filtered through 0.22 μm membrane filter, filled into 2 ml ampules and sealed, sterilized at 100° C. for 30 min. Asafetida injection was obtained in 2 ml: 1 g/ampule.

1. Animal Experiment: Promoting Abstinence Experiment of Morphine-Dependent Mouse Design of experimental method: referring to "Pharmacological Experimental Method" and "Guideline of Opioid Detoxifying Pharmaceutical Pharmacodynamics" edited by Shuyu Xu. The experiment applied dosage-increasing method to develop a morphine-dependent model and use naloxone to promote abstinence, in order to evaluate the therapeutical effect of asafetida injection in promoting abstinence of morphine-dependent mouse.

1.1 Objective: Observing the Therapeutical Effect of Asafetida Injection in Promoting Abstinence of Morphine-Dependent Mouse.

1.2. Experimental Materials and Animals

Asafetida injection: colorless and transparent liquid or emulsion (intravenous injection), 0.5 g/ml, provided by Sichuan Linqiong Company, lot no. 010401, diluted with physiological saline to desired concentration.

Morphine injection: colorless transparent liquid, Liao Wei Yao Zhun Zi (1996) No. 002747, 10 mg/ampule, produced by Shenyang First Pharmaceutical Factory, lot No. 001008.

Naloxone injection: colorless transparent liquid, Wei Yao Zhun Zi (90) No. X-100, 0.4 mg/ampule, produced by Beijing Sihuan Medical Technical Co. Ltd., lot no. 010228.

Phenoxyimidazoline hydrochloride tablet (clonidine): white tablet, Shan Wei Yao Zhun Zi (1993) No. 001321, 0.1 mg/tablet, produced by Joint Venture Shanxi Xiyue Pharmaceutical Co. Ltd., lot No. 000111.

Adult healthy Wistar rat: male and female (half and half), body weight 160-200 g, provided by Experimental Animal Center of Sichuan University (west part) and in accordance with first order quality requirement. Certificate of approval: Sichuan Experimental Animal Administration Quality Order No. 71, qualified in 1998.

1.3. Experimental Method 10 rats, 5 males and 5 females, were selected from 60 rats as negative control group. The rest rats were injected subcutaneously with morphine and administrated according to their body weights. The injection volume was 0.2 ml/100 g, thrice per day, and dosage was 5 mg/kg and 10 mg/kg for 4 days, respectively, and 15 mg/kg and 20 mg/kg for 3 days, respectively. The negative control group was injected subcutaneously with physiological saline at a dosage of 0.2 ml/100 g for the same times as morphine. On the 13th day of morphine injection, 50 rats were randomly divided into 5 groups, i.e. morphine-dependent model group, clonidine-positive control group, three asafetida injection groups with dosages of 4 g/kg, 2 g/kg and 1 g/kg, respectively. Each group was injected intraperitoneally with 0.75 ml/100 g of corresponding tested drug per day, respectively. The positive control group was perfused with 1 ml/100 g clonidine, once a day for three times. Both negative control group and morphine-dependent model group were injected intraperitoneally with 0.75 ml/kg of 0.9% physiological saline. On the last night before final administration of morphine, rats were in fasting but had access to water. On the next morning, morphine was injected subcutaneously for the last time 1 hour after the rats were injected intraperitoneally or perfused with corresponding tested drugs. 40 minutes later, rats in each group were weighed and injected intraperitoneally with 4 mg/kg naloxone immediately to promote abstinence. The abstinence reaction symptoms of rats in each group within 2 hours were observed and recorded promptly, and scored according to the standard of abstinence symptoms observation shown in Table 1. The body weights of rats were weighed at 30 min and 60 min, respectively, and the scores of abstinence reaction symptoms and average body weight decreasing values were calculated for rats in each group. The morphine-dependent model group and negative control group were subjected to t-test, i.e. significance test, in order to determine whether the morphine-dependent model group was established. The results of each tested group and the morphine-dependent model group were subjected to t-test in order to determine the therapeutical effect of tested drugs in promoting abstinence symptoms of morphine-dependent rats. At the same time, three dosage groups of asafetida injection were analyzed for equivalency.

TABLE 1

The Scoring Standard of Rat Promoting Abstinence Symptoms

| Symptom | condition | score | symptom | condition | score |
|---|---|---|---|---|---|
| performance | abnormal | 2 | the autonomic | Lacrimation | 4 |
| | Highly touch | 1 | nervous | diarrhea | 4 |
| | irritated approach | 2 | system | soft stool | 4 |
| | gnash discontinuous | 0.5 | symptom | Not in form | 8 |
| | continuous | 1 | | salivate lightly | 1 |
| | | | | obviously | 2 |

1.4 Experimental Results

The experimental results demonstrate the score of performance and autonomic nervous system symptom and the decreasing value of body weight at respective time points in morphine-dependent model group were significantly different from those of negative control group. In addition, all of the three dosage groups of asafetida injection (4 g/kg, 2 g/kg, 1 g/kg) inhibited performance such as abnormal posture, irritation, gnash and autonomic nervous system symptoms such as lacrimation, diarrhea and salivation of rats to different degrees. During the 90 minutes after administering naloxone wherein abstinence symptoms were most apparent, the sum of above two scores had significant difference compared with that of morphine-dependent model group (P<0.05-0.001). The results are shown in Table 2. Moreover, the three dosage groups of asafetida injection (4 g/kg, 2 g/kg, 1 g/kg) also significantly inhibited body weight decrease of rats at 30 min and 60 min after administering naloxone (P<0.05-0.001). The results are shown in Table 3.

TABLE 2

Effect of asafetida injection on the score of promoting abstinence performance and autonomic nervous system symptoms of morphine-dependent rats.

| Group and administration (dosage/body weight) | Number of Animals | Scores of performance and autonomic nervous system symptoms of rats at each time point after naloxone administration | | | | | |
|---|---|---|---|---|---|---|---|
| | | 15 min | 30 min | 45 min | 60 min | 90 min | 120 min |
| Negative control group | 10 | 0 | 0 | 0 | 0 | 0 | 0 |
| Morphine-dependent model group | 10 | 9.09 ± 2.45▲ | 11.92 ± 2.82▲ | 11.06 ± 2.38▲ | 9.64 ± 2.46▲ | 6.37 ± 2.58▲ | 3.33 ± 2.82▲ |
| clonidine group (0.1 mg/kg) | 10 | 2.22 ± 2.29*** | 2.68 ± 1.81*** | 1.21 ± 1.80*** | 1.61 ± 1.54*** | 0.40 ± 0.68*** | 0 ± 0*** |
| asafetida injection group (1 g/kg) | 10 | 105.72 ± 3.27* | 6.67 ± 3.80** | 8.22 ± 2.00* | 7.67 ± 4.17 | 4.89 ± 3.67 | 2.11 ± 2.47 |
| asafetida injection group (2 g/kg) | 10 | 7.39 ± 3.92 | 3.44 ± 4.17*** | 3.11 ± 3.79*** | 4.33 ± 4.96** | 2.78 ± 3.09 | 0 ± 0*** |
| asafetida injection group (4 g/kg) | 10 | 4.06 ± 410*** | 5.72 ± 4.04*** | 3.28 ± 3.23*** | 0.78 ± 1.18**□ | 0.89 ± 2.58*** | 0 ± 0*** |

TABLE 3

The effect of asafetida injection on promoting abstinence body weights of morphine-dependent rats (X ± S)

| Group and administration (dosage/body weight) | Number of Animals | body weight decreasing at 30 min after administrating naloxone (g) | body weight decreasing at 60 min after administrating naloxone (g) |
|---|---|---|---|
| Negative control group | 10 | 0.18 ± 0.213 | 0.42 ± 0.297 |
| Morphine-dependent model group | 10 | 8.182 ± 3.812ʲ | 11.531 ± 5.924ʲ |
| clonidine group (0.1 mg/kg) | 10 | 4.077 ± 3.431* | 5.560 ± 4.960* |
| asafetida injection group (1 g/kg) | 10 | 3.389 ± 4.149* | 4.221 ± 4.248** |
| asafetida injection group (2 g/kg) | 10 | 1.632 ± 2.175*** | 4.621 ± 1.818** |
| asafetida injection group (4 g/kg) | 10 | 2.874 ± 3.251** | 4.242 ± 3.605** |

In the Tables 2 and 3:
ʲ: denoting $P < 0.001$ when compared with negative control group.
*, , *: denoting $P < 0.05$, $P < 0.01$, $P < 0.00$, respectively, when compared with morphine-dependent model group.

1.5 Summary

The experimental results demonstrate asafetida injection can significantly inhibit abstinence reaction compared with morphine model group, wherein asafetida injection (4 g/kg, 2 g/kg, 1 g/kg) can significantly inhibit symptoms of rats such as abnormal posture, irritation, gnash, lacrimation, diarrhea and salivate within 120 minutes after administrating naloxone ($P<0.05$-$0.001$); and all of asafetida injection (4 g/kg, 2 g/kg, 1 g/kg) can significantly inhibit body weight decreasing of rats ($P<0.05$-$0.001$).

2. Clinical Trial 2.1 Criteria for Evaluation of Therapeutical Effect

The typical performance of abstinence syndrome was as follows: yawning, lacrimation, perspiring, bad mood, anxiety, and dysphoria.

Apparently effective: the abstinence syndrome disappears completely and performance is normal.

Effective: the abstinence syndrome is obviously abated.

Ineffective: the abstinence syndrome has no obvious remission or no remission at all.

2.2 Therapeutic Scheme

The subjects addicted to drugs were randomly grouped into asafetida injection treatment group, phenoxyimidazoline hydrochloride positive control group, placebo negative control group, wherein the phenoxyimidazoline hydrochloride is a relatively effective medicine for abstinence of drugs at present. The pharmaceuticals and usage thereof in each group were as follows:

Asafetida injection, 2 ml (equivalent to 1 g of original crude material)/bottle, thrice per day, a bottle per time, injected intramuscularly, for three consecutive days.

Phenoxyimidazoline hydrochloride, 0.1 mg/tablet, thrice per day, a tablet per time, for three consecutive days.

Placebo (physiological saline), 2 ml/bottle, thrice per day, a bottle per time, injected intramuscularly, for three consecutive days.

The results are shown in Table 4.

TABLE 4

Clinical effect of asafetida injection, phenoxyimidazoline hydrochloride, placebo on the abstinence treatment of subjects taking addictive drugs

| | | item | | | | | |
|---|---|---|---|---|---|---|---|
| | | Apparently effective | | Effective | | Ineffective | |
| group | Number of Cases | Number of Cases | % | Number of Cases | % | Number of Cases | % | Total effective rate % |
| asafetida injection, treatment group | 20 | 18 | 90.00 | 2 | 10.00 | 0 | 0 | 100 |
| phenoxyimidazoline hydrochloride, positive control group | 20 | 13 | 65.00 | 7 | 35.00 | 0 | 0 | 100 |
| Placebo, negative control group | 20 | 0 | 0 | 0 | 0 | 20 | 100 | 0 |

2.3 Conclusion

The result shown in Table 4 demonstrate asafetida injection is very effective in the abstinence treatment of common subjects taking addictive drugs.

Asafetida injection, 5 ml (equivalent to 2.5 g of original crude material)/bottle, thrice per day, a bottle per time, injected intravenously, for three consecutive days.

Phenoxyimidazoline hydrochloride, 0.1 mg/tablet, thrice per day, a tablet per time, for three consecutive days.

The results are shown in Table 5.

TABLE 5

Clinical effect of asafetida injection, phenoxyimidazoline hydrochloride on the abstinence treatment of subjects taking addictive drugs

| | | item | | | | | |
|---|---|---|---|---|---|---|---|
| | | Apparently effective | | Effective | | Ineffective | |
| group | Number of Cases | Number of Cases | % | Number of Cases | % | Number of Cases | % | Total effective rate % |
| asafetida injection, treatment group | 25 | 22 | 88.00 | 3 | 12.00 | 0 | 0 | 100 |
| phenoxyimidazoline hydrochloride, positive control group | 25 | 15 | 60.00 | 10 | 40.00 | 0 | 0 | 100 |

2.4 Typical Case

Body dependence of heroin is the strongest among drugs and its abstinence syndrome is also the strongest. Subjects addicted to heroin for over 10 years were selected for clinical treatment.

The typical performance of abstinence syndrome was as follows: yawning, lacrimation, perspiring, bad mood, anxiety, dysphoria, gooseflesh, chills, flaccidity, general aching and muscular twitching.

2.4.1 Therapeutic Scheme

The subjects addicted to drugs were randomly grouped into asafetida injection treatment group, phenoxyimidazoline hydrochloride positive control group. The pharmaceuticals and usage thereof in both groups were as follows:

2.4.2 Conclusion

The results shown in Table 5 demonstrate asafetida injection administered intravenously was also effective in the abstinence treatment of subjects deeply addicted to drugs over a long period of time. The asafetida extract of the present invention showed good effect on both moderate and serious drug addicts.

In summary, the present invention develops a new medical application of asafetida extract, and exploits a new area for the use of asafetida extract. The medicine for abstinence of drugs prepared with asafetida extract according to the present invention is effective in the abstinence treatment of subjects and has no toxicity and side effect. The medicine can be produced in a large scale and the use of modern preparation technology may cover up or weaken the special odor of asafetida. Dosage form may be selected from injection, capsule, drop pill, tablet, granule, powder, oral liquid and the like, which functions quickly and is easy to administrate.

The medicine for abstinence of drugs prepared with asafetida extract according to the present invention is suitable for the use in the abstinence treatment of subjects addicted to opioid, morphine, marijuana, diamorphine and the like.

The present invention is further described in detail in reference to following examples.

(The preparation methods of *Ferula sinkiangensis* K. M. Shen or *Ferula fukanensis* K. M. Shen and *F. assafoetida* L are same and the following examples take *Ferula sinkiangensis* K. M. Shen or *Ferula fukanensis* K. M. Shen for example)

EXAMPLE 1

The Medicine for Abstinence of Drugs Prepared with Asafetida Extract by Conventional Method: Asafetida Injection.

Asafetida extract (volatile oil) was prepared by conventional water vapor distillation, azeotropic distillation and separated with oil-water separator. 2000 ml of purified water was added to 500 g *Ferula sinkiangensis* K. M. Shen or *Ferula fukanensis* K. M. Shen, and water vapor distillation was performed at 105-108° C. 60 g volatile oil, i.e. asafetida extract, was collected after oil-water separation. 6 g 2,3-HP, β-CD was added to the asafetida volatile oil and suitable amount of water for injection was further added. After agitating for 5 minutes, 7 g NaCl (for injection) was then added. Water for injection was added to 1000 ml (equivalent to 0.5 g/ml asafetida crude material) and agitation was continued for 5 minutes. Resulting solution was adjusted to pH=5.35, filtered through 0.22 μm membrane filter, filled into 5 ml ampules and sealed. Asafetida injection was obtained after sterilizing at 100° C. for 45 min. The ingredients, contents and pH of asafetida injection were shown in Table 6 (1-05).

EXAMPLE 2

The Medicine for Abstinence of Drugs Prepared with Asafetida Extract by Conventional Method: Asafetida Injection.

Asafetida extract was prepared by conventional water vapor distillation. 2000 ml purified water was added to 500 g *Ferula sinkiangensis* K. M. Shen or *Ferula fukanensis* K. M. Shen, and water vapor distillation was performed. 2000 ml forerunning liquid was collected and redistillation was conducted. 1000 ml redistillation liquid, i.e. asafetida extract (equivalent to 0.5 g/ml asafetida crude material), was obtained after collection. After agitating for 5 minutes, 7 g NaCl (for injection) were then added. Water for injection was added to 1000 ml and agitation was continued for 5 minutes. Resulting solution was adjusted to pH=5.42, filtered through 0.22 μm membrane filter, filled into 5 ml ampules and sealed. Asafetida injection was obtained after sterilizing at 100° C. for 30 min. The ingredients, contents, and pH of asafetida injection were shown in Table 6 (1-05).

The above asafetida extracts were analyzed by GC-MS detection at Chengdu Analytic and Test Center of Chinese Academy of Sciences. The results demonstrated all of these asafetida extracts consisted essentially of α-pinene, α-terpinene, 2-borneol, terpin-4-ol, D-fenchyl alcohol, pinocarveol, β-ocimene A, β-ocimene B, di-sec-butyl disulfide, sec-butyl-trans-1-butenyl disulfide, sec-butyl-cis-propenyl disulfide, sec-butyl-cis-1-butenyl disulfide, sec-butyl-trans-2-butenyl disulfide and thio-sec-butyl-trans-methylethylene disulfide.

Sterilization temperature: 1-2 ml ampule, 100° C., 30 min; 5-10 ml ampule, 100° C., 45 min. Specification: 2 ml (1 g)/ampule; 5 ml (3 g)/ampule; 10 ml (3 g)/ampule.

The obtained asafetida injection may be administrated intramuscularly or intravenously.

The ingredients and their contents in asafetida injection, pH were shown in Table 6. (Water for injection is added as required.)

TABLE 6

Ingredients, contents, and pH of asafetida injection

| Example No. | Asafetida extract (equivalent to asafetida crude material, g/ml) | 2,3-HP, β-CD, g | NaCl, g | pH |
|---|---|---|---|---|
| 1-01 | 0.1 | 0.0012 | 0.007 | 4~6 |
| 1-02 | 0.2 | 0.0024 | 0.007 | 4~6 |
| 1-03 | 0.3 | 0.0036 | 0.007 | 4~6 |
| 1-04 | 0.4 | 0.0048 | 0.007 | 4~6 |
| 1-05 | 0.5 | 0.0060 | 0.007 | 4~6 |
| 1-06 | 0.6 | 0.0072 | 0.007 | 4~6 |
| 1-07 | 0.7 | 0.0084 | 0.007 | 4~6 |
| 1-08 | 0.8 | 0.0096 | 0.007 | 4~6 |
| 1-09 | 0.9 | 0.0108 | 0.007 | 4~6 |
| 1-10 | 1.0 | 0.012 | 0.007 | 4~6 |
| 1-11 | 1.1 | 0.0132 | 0.007 | 4~6 |
| 1-12 | 1.2 | 0.0144 | 0.007 | 4~6 |
| 1-13 | 1.3 | 0.0156 | 0.007 | 4~6 |
| 1-14 | 1.4 | 0.0168 | 0.007 | 4~6 |
| 1-15 | 1.5 | 0.018 | 0.007 | 4~6 |
| 1-16 | 1.6 | 0.0192 | 0.007 | 4~6 |
| 1-17 | 1.7 | 0.0204 | 0.007 | 4~6 |
| 1-18 | 1.8 | 0.0216 | 0.007 | 4~6 |
| 1-19 | 1.9 | 0.0228 | 0.007 | 4~6 |
| 1-20 | 2.0 | 0.024 | 0.007 | 4~6 |

EXAMPLE 3

The Medicine for Abstinence of Drugs Prepared with Asafetida Extract by Conventional Method: Asafetida Injection.

Asafetida extract was prepared by conventional azeotropic distillation. 8000 ml purified water was added to 1000 g *Ferula sinkiangensis* K. M. Shen or *Ferula fukanensis* K. M. Shen and azeotropic distillation was performed at 105-108° C. 4000 ml forerunning liquid was collected and redistillation was performed. About 2000 ml redistillation liquid, i.e. asafetida extract (equivalent to 0.5 g/ml asafetida crude material), was obtained after collection. The physicochemical properties and main ingredients of above asafetida extract were same as those in Examples 1 and 2.

6 g 2,3-HP, β-CD was added to 1000 ml asafetida extract (equivalent to 0.5 g/ml asafetida crude material). After agitating for 5 minutes, 7 g NaCl (for injection) was then added. Water for injection was added to 1000 ml and agitation was continued for 5 minutes. Resulting solution was adjusted to pH=5.40, filtered through 0.22 μm membrane filter, filled into 2 ml ampules and sealed. Asafetida injection was obtained after sterilizing at 100° C. for 30 min. The asafetida injection may be made into 2 ml: 1 g/ampule, 5 ml: 2.5 g/ampule, 10 ml: 5 g/ampule and the like. The ingredients, contents, and pH of asafetida injection were shown in table 6 (1-05).

EXAMPLE 4

The Medicine for Abstinence of Drugs Prepared with Asafetida Extract by Conventional Method: Asafetida Injection.

Asafetida extract was prepared by conventional vacuum distillation. 4000 ml purified water was added to 500 g *Ferula sinkiangensis* K. M. Shen or *Ferula fukanensis* K. M. Shen and vacuum distillation was performed at 104-107° C. and pressure of 1300-1400 Pa. 2000 ml forerunning liquid was collected and redistillation was performed. About 1000 ml redistillation liquid, i.e. asafetida extract (equivalent to 0.5 g/ml asafetida crude material crude material), was obtained after collection. The physicochemical properties and main ingredients of above asafetida extract were same as those in Examples 1 and 2.

6 g 2,3-HP, β-CD was added to 1000 ml asafetida extract (equivalent to 0.5 g/ml asafetida crude material). After agitating for 5 minutes, 7 g NaCl (for injection) was then added. Water for injection was added to 1000 ml and agitation was continued for 5 minutes. Resulting solution was adjusted to pH=5.45, filtered through 0.22 μm membrane filter, filled into 2 ml ampules and sealed. Asafetida injection was obtained after sterilizing at 100° C. for 30 min. The ingredients, contents, and pH of asafetida injection were shown in table 6 (1-05).

EXAMPLE 5

The Medicine for Abstinence of Drugs Prepared with Asafetida Extract by Conventional Method: Asafetida Injection Asafetida extract was prepared by conventional solvent extraction. 2000 g ethanol and 1000 g chloroform were added to 500 g *Ferula sinkiangensis* K. M. Shen or *Ferula fukanensis* K. M. Shen. Reflux extraction was performed at 65-70° C. for 2 hours. When the temperature of refluxing liquid dropped to room temperature, the refluxing liquid was discharged and organic solvents were recovered to obtain crude volatile oil. 1000 ml purified water was added to perform water vapor distillation. 2000 ml forerunning liquid was collected and then subjected to redistillation. 1000 ml redistillation liquid, i.e. asafetida extract (equivalent to 0.5 g/ml asafetida crude material), was obtained after collection. The physicochemical properties and main ingredients of above asafetida extract were same as those in Examples 1 and 2.

6 g 2,3-HP, β-CD was added to 1000 ml asafetida extract (equivalent to 0.5 g/ml asafetida crude material). After agitating for 5 minutes, 7 g NaCl (for injection) was then added. Water for injection was added to 1000 ml and agitation was continued for 5 minutes. Resulting solution was filtered through 0.22 μm membrane filter, filled into 2 ml ampules and sealed. Asafetida injection was obtained after sterilizing at 100° C. for 30 min. The ingredients, contents, and pH of asafetida injection were shown in table 6 (1-05).

EXAMPLE 6

The Medicine for Abstinence of Drugs Prepared with Asafetida Extract by Conventional Method: Asafetida Capsule 12 kg of asafetida extract (volatile oil, equivalent to 100 kg of asafetida crude material) and 47.74 kg of excipient were used, i.e. the weight ratio of asafetida extract and excipient was 1: 3.98, wherein the excipient was consisted of 25 kg of starch, 12 kg of compressible starch, 8 kg of L-HPC, 2.5 kg of microcrystalline cellulose, and 0.24 kg of CMS-Na. Excipient was placed into agitator and agitated for 5 min, then asafetida volatile oil was sprayed uniformly into excipient and agitation was continued for 5 min. 5% starch slurry was added to make a soft material, which was placed into a granulator and filtered through stainless steel sieve to form wet granules. The wet granules were dried below 60° C. and obtained dry granules were put into granulator again and filtered through stainless steel sieve to adjust the granules. 0.096 kg of magnesium stearate was added and the weight ratio of excipient and lubricant was 1: 0.002. Dry granules after adjustment were put into agitator and lubricant is added and mixed for 5 min, then asafetida capsules were made in a full automatic capsule filling machine. Asafetida extract in each asafetida capsule was equivalent to 0.5 g asafetida crude material.

EXAMPLE 7

The Medicine for Abstinence of Drugs Prepared with Asafetida Extract by Conventional Method: Asafetida Drop Pill (i.e. Asafetida Pill)

Volatile oil was prepared by conventional water vapor distillation, and 12 kg of asafetida extract (volatile oil) was obtained after the separation in oil-water separator, which was equivalent to 100 kg of asafetida crude material. (1) The ratio of gelatin:glycerol:water was 1:0.3-0.5:0.7-1.4. Gelatin was swelled in a suitable amount of water (25% weight of gelatin). On the other hand, glycerol and water were placed into stainless steel pot, heated to 70-80° C., and mixed homogeneously. Swelled gelatin was added and melt into a homogeneous solution. After incubation for 1-2 hours, the solution was settled and filtered through nylon cloth after removing supernatant foam. (2) Preparing drug solution (i.e. oil solution): 0.75 g vegetable oil (e.g. peanut oil) was added to above asafetida volatile solution and mixed thoroughly. (3) Preparing drop pill: gelatin solution and drug solution were added to the storage tank of dropping pill machine, respectively. Quantitative gelatin and drug solutions passed through a bilaminar nozzle via quantitative controller, wherein gelatin solution at 60-70° C. was transmitted into outer layer and drug solution was transmitted into inner layer. The drug solution was encapsulated by the gelatin and asafetida extract in each asafetida pill was equivalent to 0.25 g asafetida crude material. Encapsulated pills were then dropped into coolant, i.e. liquid paraffin at 13-17° C. The liquid drops formed spherical shape because of surface tension, gradually solidified into gelatin pills, and collected in collector. (4) Adjustment and drying: Firstly, liquid paraffin attached onto gelatin pills was wiped with gauze. The gelatin pills were blown at about 10° C. for 4-6 hours, dried at 25-35° C. for 4 hours, taken out, washed twice with a mixed solution of ethanol/acetone (5:1), and then dried at 40-45° C. for 24 hours after the wash solution was blown to dryness. After checking with lamp and removing inferior products, the pills were washed once with 95% ethanol and blown to dryness at 40-45° C. Asafetida gelatin (i.e. soft capsule) was thereby obtained.

EXAMPLE 8

The Medicine for Abstinence of Drugs Prepared with Asafetida Extract by Conventional Method: Asafetida Tablet 12 kg of asafetida extract (volatile oil, equivalent to 100 kg of asafetida crude material) and 42.7 kg of excipient were used, i.e. the weight ratio of asafetida extract and excipient was 1: 3.56, wherein the excipient was consisted of 22.5 kg of starch, 11.5 kg of compressible starch, 6.5 kg of L-HPC, 2 kg of microcrystalline cellulose, and 0.2 kg of CMS-Na. Excipient was placed into agitator and agitated for 5 min, then asafetida volatile oil was sprayed uniformly into excipient and agitation was continued for 5 min. 5% starch slurry was added to make a soft material, which was placed into a granulator and filtered through stainless steel sieve to form wet granules. The wet granules were dried below 60° C. and obtained dry granules were put into granulator again and filtered through stainless steel sieve to adjust the granules. 0.214 kg of magnesium stearate was added and the weight ratio of excipient and lubricant was 1:0.005. Dry granules after adjustment were put into agitator and lubricant is added and mixed for 5 min, then asafetida tablets were made in a tablet machine. The asafetida tablets were then put into a coating machine to form film coating. Asafetida extract in each asafetida tablet was equivalent to 0.5 g asafetida crude material.

EXAMPLE 9

The Medicine for Abstinence of Drugs Prepared with Asafetida Extract by Conventional Method: Asafetida Granule 12 kg of asafetida extract (volatile oil, equivalent to 100 kg of asafetida crude material) and 196 kg of excipient were used, i.e. the weight ratio of asafetida extract and excipient was 1:16.33, wherein the excipient was consisted of 140 kg of starch and 56 kg of dextrin. Excipient was placed into agitator and agitated for 5 min, then asafetida volatile oil was sprayed uniformly into excipient and agitation was continued for 5 min. 5% starch slurry was added to make a soft material, which was placed into a granulator and filtered through stainless steel sieve to form wet granules. The wet granules were dried below 60° C. and obtained dry granules were put into granulator again and filtered through stainless steel sieve to adjust the granules. Dry granules after adjustment were packed. Asafetida extract in each package of asafetida was equivalent to 0.5 g asafetida crude material.

EXAMPLE 10

The Medicine for Abstinence of Drugs Prepared with Asafetida Extract by Conventional Method: Asafetida Powder 12 kg of asafetida extract (volatile oil, equivalent to 100 kg of asafetida crude material) were used. 140 kg of starch and 36 kg of sucrose powder were placed into agitator and agitated for 5 min, then asafetida volatile oil was sprayed uniformly into adjuvant and agitation was continued for 5 min. Discharged material were dried below 60° C., crushed and filtered through 100 mesh. 20 kg of talc powder were added, mixed in agitator for 15 min, and packed in quantitative powder sub packaging machine. Asafetida extract in each package of asafetida was equivalent to 0.5 g asafetida crude material.

EXAMPLE 11

The Medicine for Abstinence of Drugs Prepared with Asafetida Extract by Conventional Method: Asafetida Oral Liquid Volatile oil was extracted with oil-water separator by water vapor distillation. 300 g 2,3-HP, β-CD was added to 3 kg of asafetida extract equivalent to 25 kg of asafetida. A suitable amount of distilled water was added and agitated for 5 min. 25 kg of 50% curate syrup was added and suitable amount of distilled water was added to 125,000 ml. After agitating for 5 min, the solution was filtered through 0.45 μm membrane filter to produce asafetida oral liquid. The obtained oral liquid was filled and sealed in a full automatic oral liquid filling machine (10 ml/bottle). Asafetida oral liquid was obtained after sterilizing at 100° C. for 45 min. Specification: 10 ml, 2 g/bottle.

What is claimed is:

1. A method for abstinence of drugs which bind with morphine receptor, which comprises administering a therapeutically effective amount of asafetida extract to a subject in need thereof, wherein the asafetida extract is a volatile oil extracted by distillation from factice resin of *Ferula sinkiangensis* K. M. Shen, *Ferula fukanensis* K. M. Shen, or *Ferula assafoetida* L. from Iran and Afghanistan.

2. The method according to claim 1, wherein the asafetida extract is in a form selected from the group consisting of injection, capsule, drop pill, tablet, granule, powder, and oral liquid.

3. The method according to claim 1, wherein the asafetida extract is extracted from factice resin of *Ferula sinkiangensis* K. M. Shen or *Ferula fukanensis* K. M. Shen, the asafetida extract consisting essentially of α-pinene, α-terpinene, 2-borneol, terpin-4-ol, D-fenchyl alcohol, pinocarveol, β-ocimene A, β-ocimene B, di-sec-butyl disulfide, sec-butyl-trans-1-butenyl disulfide, sec-butyl-cis-propenyl disulfide, sec-butyl-cis-1-butenyl disulfide, sec-butyl-trans-2-butenyl disulfide and thio-sec-butyl-trans-methylethenyl disulfide.

4. The method according to claim 1, wherein the asafetida extract is extracted from factice resin of *F. assafoetida* L from Iran and Afghanistan, the asafetida extract consisting essentially of α-pinene, 2-borneol, terpin-4-ol, D-fenchyl alcohol, pinocarveol, dimethyl disulfide, dimethyl trisulfide, methyipropenyl disulfide, 2,2-dimethyithiopropane, 1,2-diethylthiopropane, N,N-dimethylthioformamide and propenylbutyl disulfide.

* * * * *